United States Patent
Smith et al.

(10) Patent No.: US 6,447,446 B1
(45) Date of Patent: Sep. 10, 2002

(54) METHOD AND APPARATUS FOR CLEANING AN ENDOSCOPE LENS

(75) Inventors: Aaron C. Smith; Gary F. Peters, both of Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/432,093

(22) Filed: Nov. 2, 1999

(51) Int. Cl.[7] ............................................. A61B 1/015
(52) U.S. Cl. ..................... 600/157; 600/159; 600/118
(58) Field of Search ......................... 600/121, 155–159, 600/118

(56) References Cited

U.S. PATENT DOCUMENTS

| | | | | |
|---|---|---|---|---|
| 5,022,382 A | * | 6/1991 | Ohshoji et al. | 600/156 |
| 5,339,800 A | * | 8/1994 | Wiita et al. | 600/157 |
| 5,400,767 A | * | 3/1995 | Murdoch | 600/157 |
| 5,402,770 A | * | 4/1995 | Iida et al. | 600/159 |
| 5,575,756 A | * | 11/1996 | Karasawa et al. | 600/157 |
| 5,908,296 A | * | 6/1999 | Kipke et al. | 433/80 |
| 6,110,103 A | * | 8/2000 | Donofrio | 600/157 |
| 6,126,592 A | * | 10/2000 | Proch et al. | 600/158 |

* cited by examiner

Primary Examiner—John P. Leubecker

(57) ABSTRACT

An endoscope lens cleaning system for use in removing surgical debris from the objective lens of an endoscope has a sheath adapted to receive the endoscope, carrying a control switch and having an open distal end in fluid communication with a proximally mounted luer lock for removably engaging the distal luer connection of a tubing set. The tubing set is connected to and engaged with a peristaltic pump including a microprocessor or controller adapted to respond to actuation of the control switch and execute software including program steps for operation of the pump. The pump controller is programmed to execute a scrub cycle each time the clinician actuates the control switch mounted on the preferably disposable sheath. Scrub cycles are executed in a sequence of steps including a forward or outflow motion of the pump to dispense a first selected volume of irrigation fluid through the sheath and over the endoscope objective lens; a brief pause follows, to allow any residual fluid pressure to dissipate, and a reverse or inflow motion of the pump next withdraws or retracts any residual fluid droplets from the endoscope objective lens and into the sheath. The pump controller is programmed to perform two normal scrub cycles followed by a clear or purge cycle wherein the forward portion of the cycle dispensing irrigation fluid over the endoscope objective lens is longer than usual, thereby flushing any residual body fluids, other surgical debris or air from the sheath and restoring optimal lens cleaning system performance. The finger activated control switch is preferably releasably mounted directly on a disposable sheath, as opposed to being incorporated in a foot pedal.

17 Claims, 6 Drawing Sheets

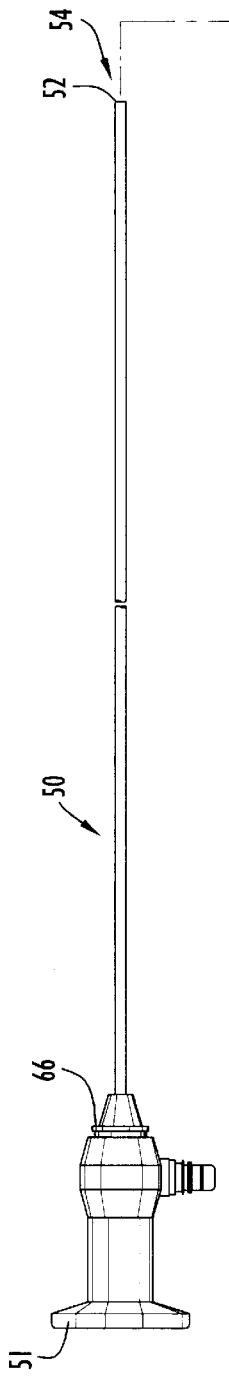
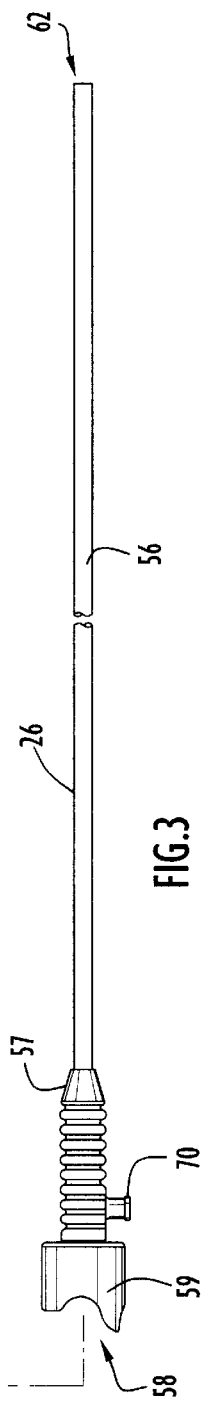
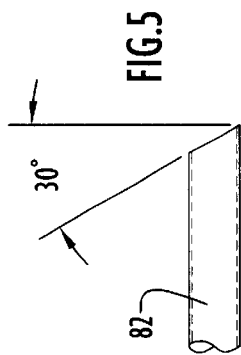
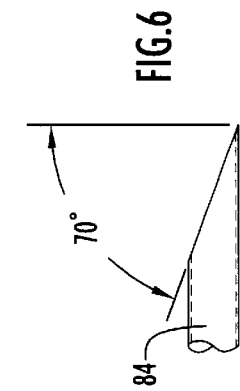
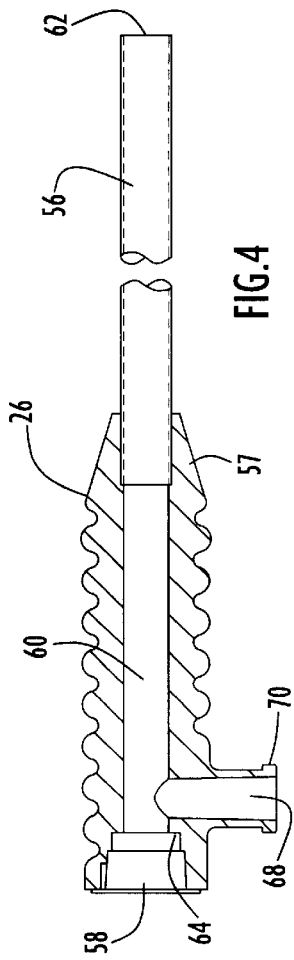

METHOD AND APPARATUS FOR CLEANING AN ENDOSCOPE LENS

CROSS-REFERENCE TO RELATED APPLICATIONS

The instant application is related to U.S. patent application Ser. No. 08/071,912 filed Jun. 3, 1993, now abandoned, U.S. patent application Ser. No. 08/095,975 filed Jul. 22, 1993, U.S. patent application Ser. No. 09/129,180 filed Jun. 5, 1998, now U.S. Pat. No. 5,989,183, and U.S. patent application Ser. No. 09/093,619 filed Jun. 9, 1998, now U.S. Pat. No. 6,110,103, all entitled Disposable Endoscope Sheath, the entire disclosures of which are incorporated herein by reference.

BACKGROUND OF THE INVENTION

1. Field of the Invention

The present invention relates to a method and apparatus for cleaning endoscope lenses including a disposable endoscope sheath providing effective flushing of surgical debris from the distal viewing end of an endoscope, in the body.

2. Discussion of the Prior Art

Endoscopes permit remote viewing of a surgical site while a surgical procedure is being performed. During surgery, blood, tissue or other debris from the surgical site can splatter onto the viewing end of the endoscope, thereby impairing the field of view through the endoscope. The surgical debris obscuring the field view of the endoscope must be removed and so, using methods of the prior art, it is necessary to interrupt the procedure and remove the endoscope for cleaning, thereby unnecessarily prolonging the procedure.

Because of the inconvenience of removing and cleaning an endoscope during surgery, some surgeons prefer to use an endoscope with a sheath having a provision for flushing away surgical debris obscuring the endoscope view. Endoscope sheaths of the prior art are generally custom fitted to the endoscope and often include air tubes, water tubes or suction tubes to flush away or suction away surgical debris from the viewing end. The irrigation, suction and air tubes on the endoscope sheath often add significant girth to the profile of the endoscope, thus requiring a relatively large incision to accommodate the sheath and endoscope together. Since endoscopes are of different lengths, a variety of corresponding sheath lengths are required to provide a compatible sheath for each endoscope length.

Another problem associated with endoscope lens cleaning systems of the prior art is that often, after flushing or irrigating the distal end of the endoscope, a droplet of irrigating fluid remains on the endoscope lens, thereby providing a substantial distortion and obscuring the surgeon's field of view.

In order to overcome the problem of leftover droplets on the endoscope lens, the Xomed® Endoscrub® sheath was developed for use with the Endoscrub™ lens cleaning system, whereby a pump dispensing saline irrigation fluid is operated first in the forward direction, to provide an outward flow of irrigating fluid, followed by a short suction pulse, to retract or withdraw saline droplets clinging to the distal end of the endoscope and back into the sheath lumen or irrigation space. One problem which has been observed when using the Endoscrub® lens cleaning system, however, is that often blood or other surgical debris can also be drawn back into the sheath lumen or irrigation space where the accumulated debris may hinder later operation of the Endoscrub® lens cleaning system.

It has also been observed that a clinician may be required to change endoscopes and sheaths during a procedure, and if the irrigation fluid tubing set is attached to the sheath by conventional friction fit, it is difficult to change sheaths, and thus endoscopes, during the procedure. The tubing set is connected to the irrigation fluid pump and so it is awkward for the clinician to have to change the tubing set each time it is desired to change the endoscope to a differently dimensioned endoscope.

Another problem encountered in using the Xomed® Endoscrub® system is that use of a foot pedal to initiate the scrub cycle contributes to a proliferation of foot pedals on the operating room (OR) floor. Since many other powered instruments and sensor systems utilize foot pedals, adding a foot pedal for the endoscope system to the existing clutter on the OR floor makes it that much more difficult to control the lens cleaning system.

Another problem associated with endoscope cleaning systems utilizing peristaltic pumps is that tubing elasticity limits the precise control of the fluid dispensed at the tip of the sheath. If the tubing is made from a more pliable durometer material, the tubing set is more amenable to use in a peristaltic pump, however, the more pliable durometer tubing also blows up or expands in response to pressurization during pumping and is provides less control over the exact volume of fluid dispensed at the endoscope tip. Ideally, tubing supplying saline to the endoscope distal end through the peristaltic pump would not comprise the ability of the pump controller to control the volume and timing of fluid dispensed at the endoscope tip.

There is a need for a method and apparatus for cleaning the distal end of an endoscope which overcomes the problems associated with the prior art.

OBJECTS AND SUMMARY OF THE INVENTION

Accordingly, it is a primary object of the present invention to overcome the problems associated with the prior art by providing an endoscope lens cleaning system having an endoscope sheath, tubing set and software controlled pump providing a pre-programmed sequence of scrub cycles consisting of a flush intervals with forward actuation of the pump to dispense irrigation fluid over the endoscope lens for a selected duration, a brief pause interval to allow any residual pressure to dissipate, and a suction pulse interval with reverse actuation of the pump to retract any droplets of fluid remaining on the lens into the sheath lumen or irrigation space.

A further object of the present invention is to eliminate the problem of accumulated surgical debris within the sheath lumen or irrigation space, restoring optimal cleaning performance, by executing a purge cycle every third scrub cycle, where the purge cycle includes an extra long flush interval, flushing any residual body fluids, debris or air from the sheath lumen.

An additional object of the present invention is to provide an easily connected fluid path including a fluid tight, readily disconnectable luer connector, thereby permitting the irrigation tubing to be attached and detached to the sheath quickly and easily when changing endoscopes.

Another object of the present invention is providing an ideally positioned, sheath-mounted finger activated switch, thereby obviating the requirement for an additional foot pedal cluttering the OR floor.

Yet another object of the present invention is more precisely controlling the volume of irrigation fluid dispensed at the tip of the sheath with a specially adapted irrigation tubing set having lesser cross sectional elasticity.

The aforesaid objects are achieved individually and in combination, and it is not intended that the present invention be construed as requiring two or more of the objects to be combined unless expressly required by the claims attached hereto.

In accordance with the present invention, an endoscope lens cleaning system for use in removing surgical debris from the objective lens of an endoscope has a sheath adapted to receive the endoscope, carrying a control switch and having an open distal end in fluid communication with a proximally mounted luer lock for removably engaging the distal luer connection of a tubing set. The tubing set is connected to and engaged with a peristaltic pump including a microprocessor or controller adapted to respond to actuation of the control switch and execute software including program steps for operation of the pump.

In the preferred embodiment, the pump controller is programmed to execute a scrub cycle each time the clinician actuates the control switch mounted on the preferably disposable sheath. Scrub cycles are executed in a sequence of steps including a flush interval with a forward or outflow motion of the pump to dispense a first selected volume of irrigation fluid through the sheath and over the endoscope objective lens; a brief pause interval follows, to allow any residual fluid pressure to dissipate, and a suction pulse interval with a reverse or inflow motion of the pump next withdraws or retracts any residual fluid droplets from the endoscope objective lens and into the sheath lumen or irrigation space. The pump controller is programmed to perform two normal scrub cycles followed by a longer scrub cycle called a clear or purge cycle. The purge cycle differs from the ordinary or normal scrub cycle in that the flush interval dispensing irrigation fluid over the endoscope objective lens is of longer duration than in normal scrub cycles, approximately 2 seconds, thereby flushing any residual body fluids, other surgical debris or air from the sheath and restoring optimal lens cleaning system performance.

The pump is controllable in one of preferably six user selectable modes to determine flush interval forward run times according to a preprogrammed table. The pump preferably includes a separate control for enabling or disabling the clear or purge cycle. Additionally, the pump controller is programmed to respond to a continuous purge command; when the control switch is depressed and in the closed position longer than the programmed flush interval, the pump continues to run in the forward mode until the control switch is released.

Preferably, the pump controller is responsive to an eight-position rotary selection switch and provides an indicator signal to a light emitting diode (LED) or other visually perceptible indicator. The eight-position rotary selection switch provides selection of the mode of operation for the pump, corresponding to pre-programmed operating steps in the pump controller, the pump modes are: OFF, PRIME, MODE ONE, MODE TWO, MODE THREE, MODE FOUR, MODE FIVE and MODE SIX. The pump controller is programmed to illuminate the LED at any setting other than "0" or "OFF" under normal conditions. The controller running the software within the pump receives and decodes the input of the eight position rotary switch, placing the pump in a mode associated with the selected rotary switch position. As noted above, each pump mode has a unique scrub cycle including a selected flush interval duration and suction pulse duration. The pump controller detects the operation of the momentary contact control switch preferably mounted on the endoscope sheath and executes a flush interval upon sensing that the momentary contact control switch has been depressed, continuing to pump in the flushing or forward direction for as long as the control switch is depressed. When the control switch is released, the scrub cycle is completed by stopping, pausing and then operating in the reverse direction, as noted above.

Additionally, the controller controls the LED indicator, illuminating the LED to indicate pump status by remaining on when the pump is on or by flashing or blinking when an error has occurred. Finally, the controller software senses the power bus status, allowing for constant operation over a wide voltage range. The pump motor functions at only one speed regardless of the power bus voltage, thus allowing the device to operate consistently over a variety of input power conditions. If the power bus is not within acceptable limits, the LED is programmed to flash, indicating an error.

In the preferred embodiment, the irrigation tubing attaches to the sheath via a quick connect mechanism (e.g., a luer lock connector). The luer connector enables the clinician to freely change sheaths and endoscopes during a procedure, without the need to change the tubing set engaged with the pump.

The finger activated control switch is preferably releasably mounted directly on a disposable sheath, as opposed to being incorporated in a foot pedal. The sheath-mounted finger-activated switch is a normally-open spring biased momentary-contact switch electrically connected to the pump controller and is reusable and readily sterilized by autoclave or cold soaked sterilization methods.

Advantageously, the irrigation tubing set for use in the method and apparatus of the present invention has a first tubing section of pliable 50 durometer tubing in the upper portion to allow proper peristaltic pump operation and is connected in series with a second section made of more rigid 70 durometer tubing to eliminate uneccessary cross sectional elasticity. The two tubing sections are connected with a barbed conduit adapter. The distal end of the tubing set includes a luer lock adapted to receive the luer connector on the endoscope sheath. The proximal end of the tubing set includes a spike connector sheathed in a spike cover. The tubing set, as provided to the user, includes a slide clamp adapted to occlude or shut off flow of fluid flowing through the tubing.

The foregoing and additional objects, features and advantages of the invention will become apparent to those of skill in the art from the following detailed description of a preferred embodiment, taken with the accompanying drawings wherein like reference numerals in the various drawings identify like components.

BRIEF DESCRIPTION OF THE DRAWINGS

FIG. 3 is a top view, in elevation, of the disposable endoscope sheath for use in the system of the present invention and illustrates the axial alignment of an endoscope for insertion therein, in accordance with the present invention.

FIG. 4 is a partial cross-section, in elevation, of the disposable endoscope sheath of FIG. 3, in accordance with the present invention.

FIG. 5 is a side view, in elevation, of an alternative embodiment of the endoscope sheath of FIGS. 3 and 4 having an inclined or angled distal end inclined at 30° for use with angled endoscopes, in accordance with the present invention.

FIG. 6 is a side view, in elevation, of an alternative embodiment of the endoscope sheath of FIGS. 3 and 4 having an inclined or angled distal end inclined at 70° for use with angled endoscopes, in accordance with the present invention.

DESCRIPTION OF THE PREFERRED EMBODIMENT

Figure 1:
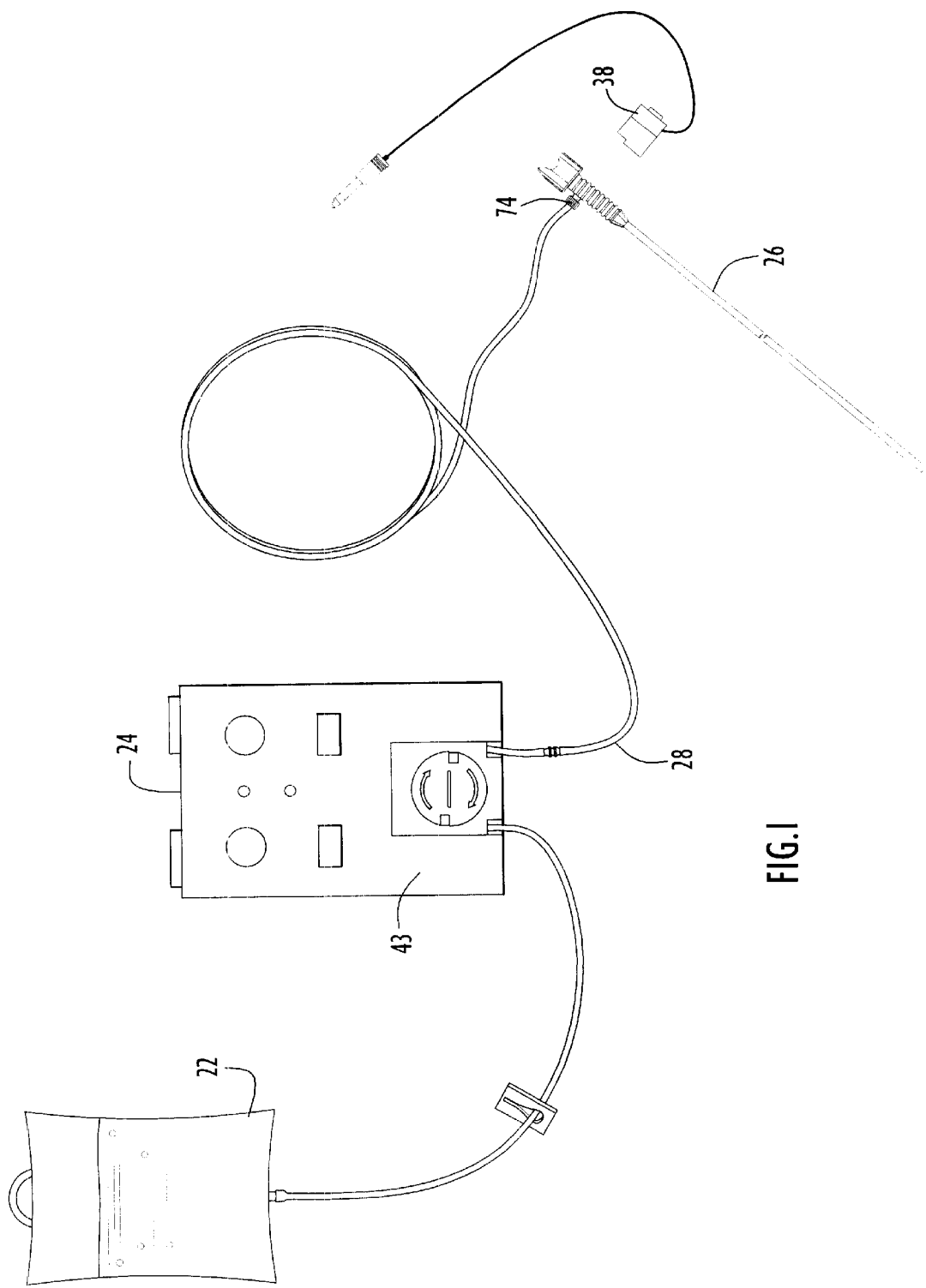
FIG. 1 is a diagram illustrating the components of the endoscope lens cleaning system in accordance with the present invention.

In accordance with the present invention and as illustrated in FIG. 1, a system 20 for cleaning an endoscope lens includes a reservoir of irrigation fluid 22, a peristaltic pump 24 and an endoscope sheath 26 in fluid communication with reservoir 22 via tubing set 28. A releasably mountable control switch 38 is preferably mounted upon and carried by endoscope sheath 26, when in use.

Figure 2:
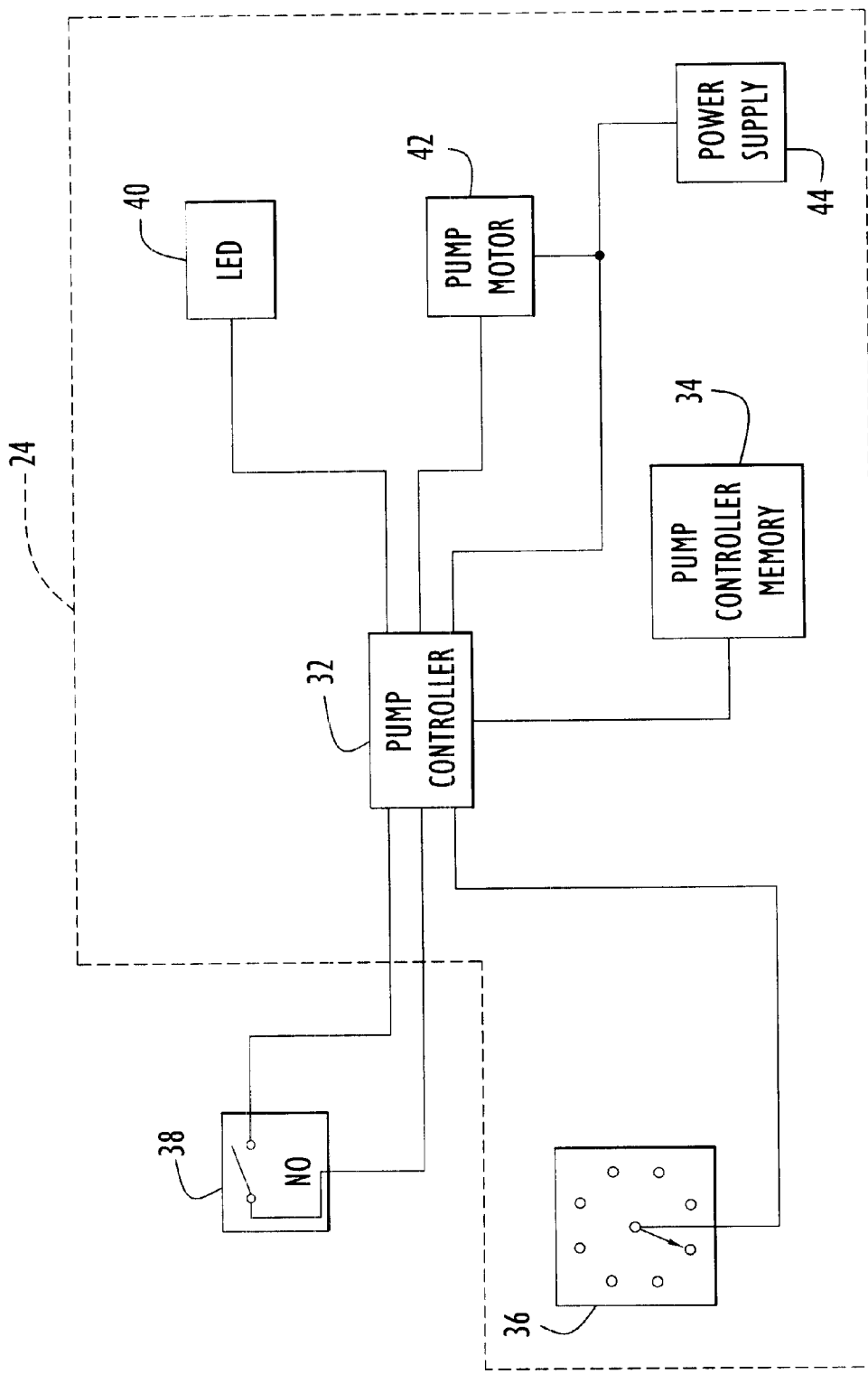
FIG. 2 is a schematic diagram illustrating connections among the components of the pump used in conjunction with the endoscope lens cleaning system in accordance with the present invention.

As best seen in FIG. 2, pump 24 includes a pump controller or microprocessor 32 operable in conjunction with a pump controller memory 34 used to store preprogrammed instructions or method steps for operating the endoscope lens cleaning system of the present invention. Pump controller 32 is responsive to normally open momentary contract control switch 38 and to the rotary eight-position mode selector switch 36, and provides an enabling signal to actuate indicator LED 40 and a pump motor enabling signal for initiating actuation of and indicating the direction of operation for pump motor 42. All of the components within pump 24 are contained within a unitary housing 43 (as shown in FIG. 1) and are energized by power supply 44. Power supply 44 is adapted to receive power from an industry standard plug for connection to a 110-volt AC mains supply. Power supply 44 is operable over a wide range of mains supply voltages and pump controller 32 and power supply 44 cooperate to operate pump motor 42 at a selected RPM, without variation in pump RPM as a result of variation in the mains supply voltage. In the event that the mains supply voltage is excessively low or excessively high, thus making it impossible to maintain the selected pump RPM, pump controller 32 is programmed to indicate an error condition by illuminating pump LED 40 in a sequence of flashes or blinks, indicating an error has occurred. In addition, pump controller 32 is programmed to continuously illuminate LED 40 when pump motor 42 is activated, to indicate pump status.

Figure 12:
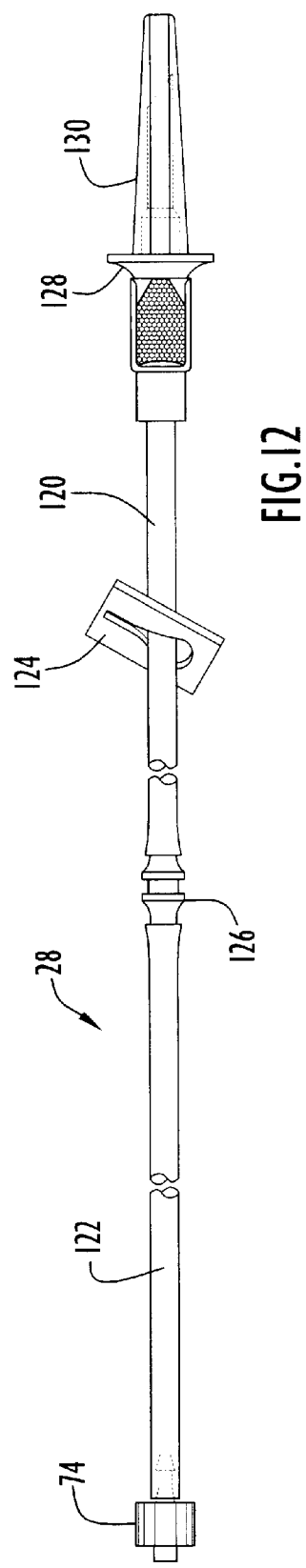
FIG. 12 is a side view, in elevation, of the tubing set having tube sections of first and second durometers, in accordance with the present invention.

Turning now to FIGS. 3 and 4, an endoscope 50 includes a proximal eye-piece 51 carrying an elongate cylindrical body or shaft terminated distally at distal end 52 carrying an objective lens 54. The proximal end of the elongate cylindrical body or shaft is terminated in a tapered segment having a shoulder 66. Endoscope sheath 26 is preferably disposable and includes an elongated vinyl sleeve member 56 joined to a distal end portion of a sleeve housing 57 that is preferably formed of plastic such as ABS. Sleeve housing 54 carries a molded ABS plastic base bonded to sheath or sleeve housing open proximal end 58. Sleeve housing 57 also carries a transversely projecting tubular member defining an intersecting transverse fluid lumen 68 terminated in a fluid-tight releasable connector such as sheath luer connector female member 70. Preferably, sheath luer connector female member 70 includes double start right-hand threads, is made in accordance with ANSI/HIMA Spec MD70.1-193, and is releasably connectable to tubing set luer connector male member 74, as best seen in FIGS. 1 and 12.

Endoscope 50 is received within endoscope sheath 26 through the sheath open proximal end 58 and extends through the sheath lumen 60 to position endoscope distal end 52 carrying endoscope objective lens 54 proximate sheath open distal end 62, defining an annular irrigation channel or irrigation space between the exterior surface of endoscope 50 and the interior surface defining sheath lumen 60. When completely inserted, the endoscope proximal shoulder 66 bears snugly against the sheath sealing surface 64, forming a fluid-tight seal at the proximal end of the assembly comprising the endoscope 50 and sheath 26. When sheath 26 and endoscope 50 are sealingly engaged, forming a seal between endoscope shoulder 66 and sheath seal surface 64, fluid from reservoir 22 pumped via tubing set 28 flows through transverse lumen 68 and distally toward the sheath open distal end 62, in the annular irrigation channel defined between the exterior surface of endoscope 50 and the interior surface defining sheath lumen 60. Endoscope 50 and sheath 26 of FIGS. 3 and 4 have transverse distal end surfaces with objective lense 54 aimed in the direction of the major axis of the endoscope and sheath.

Figure 8:
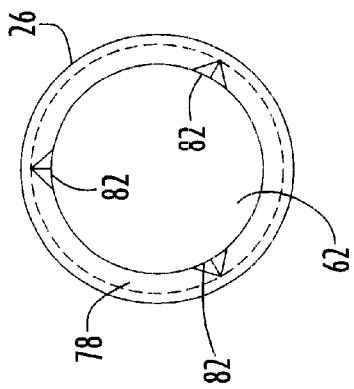
FIG. 8 is a distal end view, in elevation, of the sheath of FIG. 7, in accordance with the present invention.
Figure 7:
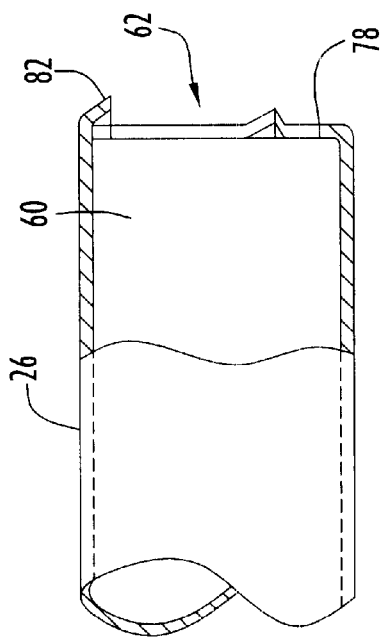
FIG. 7 is a side view in elevation and partial cross-section of the distal end of the endoscope sheath illustrated in FIGS. 3 and 4, in accordance with the present invention.

Turning now to FIGS. 7 and 8, endoscope elongate sleeve segment 56 surrounds and defines sheath lumen 60 and terminates distally in open distal end 62 which is encircled by an inwardly projecting transverse radial flange 78 for stepping or spacing the endoscope viewing end carrying objective lens 54 away from flange 78 in a predetermined retracted position to establish a distal gap of predetermined magnitude between the flange portion 78 and the viewing end of the endoscope. The distal gap is sized so that irrigating solution directed onto the irrigation channel is redirected by flange 78 to flow onto the viewing end 52 of endoscope 50 and flush surgical debris from the viewing end of the endoscope and through the distal or terminal opening at sheath open distal end 62. As noted above, the irrigation channel or space is that space between the exterior surface of the endoscope and the interior surface of the sheath sleeve member 56 defining the sheath lumen 60. The annular irrigation space is sized to retain irrigation fluid by capillary action when the irrigation fluid is no longer being pumped into the irrigation channel. In the embodiment of FIGS. 7 and 8, flange 78 has three dimples 80 equally spaced at a radial separation of 120 and projecting distally from flange 78 to direct flow of irrigation fluid from the irrigation channel onto the endoscope objective lens. Each dimple 80 includes first and second triangular planar walls intersecting to define a distally projecting radial spine to provide an inward facing, triangular, fluid dispensing opening.

Figure 10:
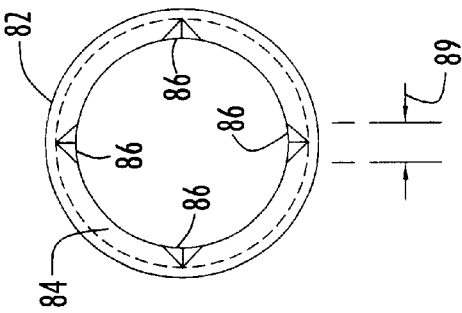
FIG. 10 is a distal end view, in elevation, of the inclined sheath of FIG. 9 in accordance with the present invention.
Figure 9:
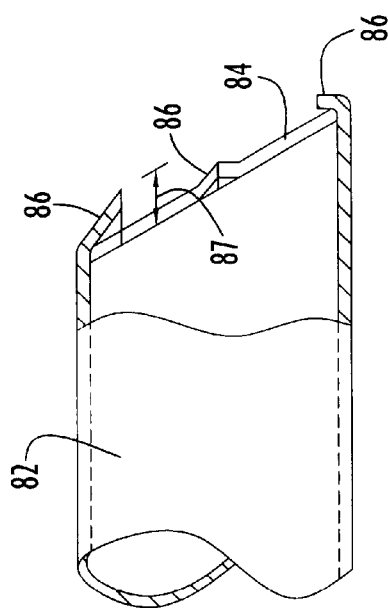
FIG. 9 is a side view in elevation and partial cross-section of the distal end of the inclined endoscope sheath of FIG. 5, in accordance with the present invention.

Turning now to FIGS. 5, 6, 9 and 10, alternative embodiments of the endoscope sheath are illustrated having inclined distal or terminal ends. Endoscopes are manufactured having objective lenses disposed at inclined angles ranging from 5° to 70°, with respect to the longitudinal axis of the endoscope. In accordance with the present invention, vinyl endoscope sleeves have terminal ends and flange portions for use with angled endoscopes; the distal portion of the sleeve is inclined at an angle ranging from 5° to 70° to the longitudinal axis of the sleeve and formed with an inwardly projecting flange portion, such that a predetermined irrigation space is defined between the sleeve and the endoscope shaft when the sleeve receives the endoscope shaft. Referring specifically to FIG. 5, inclined end sleeve 82 has an angled distal end inclined at 30°, for use with an angled endoscope. FIG. 6 illustrates the distal end cutaway angled or inclined at 70° for use with similarly angled or inclined endoscopes. Referring specifically to FIGS. 9 and 10, FIG. 9 is a partial cross section of the distal portion of inclined end sleeve 82 of FIG. 5. The distal end of the inclined end sleeve 82 is terminated in a transverse inwardly projecting flange portion such that a predetermined irrigation space is defined between the sleeve and the endoscope shaft when the sleeve receives the endoscope shaft.

Referring specifically to FIG. 5, inclined end sleeve 82 has an angled distal end cutaway or inclined at 30° for use with an angled endoscope. FIG. 6 illustrates the distal end cutaway, angled or inclined at 70° for use with similarly angled or inclined endoscopes. Referring specifically to FIGS. 9 and 10, FIG. 9 illustrates an elevation and partial cross section the distal portion of inclined end sleeve 82 from FIG. 5. The distal end of the inclined end sleeve 82 is terminated in a transverse inwardly projecting flange 84 carrying an array of, preferably, first, second, third and fourth distally projecting dimples 86 equally spaced at a radial separation of 90 about the circumference of the distal end portion, as best seen in FIG. 10, the distal end view of inclined end sleeve 82. Each dimple 86 includes first and second triangular planar walls intersecting to define an angled, distally projecting radially aligned spine to provide an inward facing, triangular, fluid dispensing opening. Preferably, each dimple 86 projects distally to define an inward facing, triangular, fluid dispensing opening with a distal extent 87 of approximately 0.20 inches. Each dimple 86 has a selected width 87 at the inner peripheral edge of flange 84; preferably, selected width is 0.030 inches.

Figure 11:
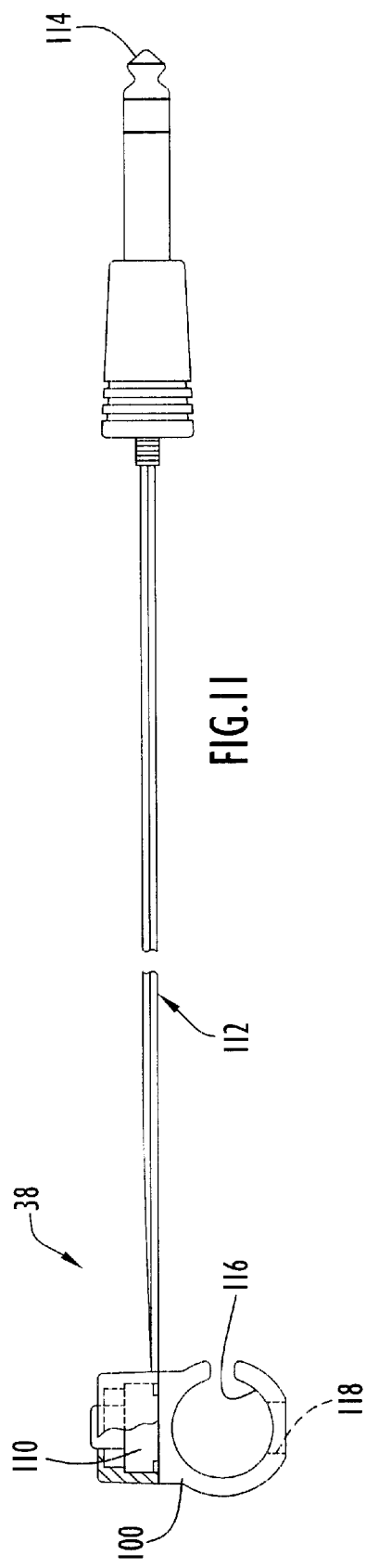
FIG. 11 is a diagrammatic illustration in partial cross-section of the sheath-mounted control switch, in accordance with the present invention.

Turning now to FIG. 11, control switch 38 comprises an assembly having a releasably attachable control switch housing 100 shown in partial cross section in FIG. 11. Control switch housing encloses and sealingly protects the momentary contact single pole spring biased normally open switch mechanism 110 having first and second poles connected to first and second wires of two-wire cable 112 which, in turn, connected at the proximal end to tip and ring connections of a two-wire connector 114 such as an RCA jack, quarter inch pin jack or the like.

Control switch housing 100 is adapted to be releasably mounted on the sleeve housing 57 on the proximal portion of endoscope sheath 26. Control switch housing 100 includes a partial cylindrical wall segment 116 sized to receive and be releasably mounted on sheath sleeve housing 57. Control switch housing partial cylindrical wall segment 116 includes a longitudinal notch 118 sized to receive the sleeve housing transversely projecting tubular member terminated in luer connector 70. Control switch 100 housing is therefor indexed by notch 118, permitting the clinician to install control switch housing 100 on sleeve housing 57 in only the one orientation which is ideally suited to operating the control switch 38. Control switch mechanism 110 is closed and actuated by depressing the switch mechanism button, thereby sending a desired control signal to the pump controller 32 as shown in FIG. 2.

FIG. 12 illustrates tubing set 28, also shown in FIG. 1, including male luer connector 74 for connection to sheath female luer connector 70. Tubing set 28 includes a first low durometer tube section 120 connected in series and in fluid communication with a second, higher durometer tube section 122 via a barbed conduit adapter 126. Preferably, first tube section 120 is made of flexible PVC tubing of 50 durometer. Second tube section 122 is preferably made of flexible PVC tubing having the same inner diameter and outer diameter dimensions and is of 50 durometer material. For purposes of nomenclature, the reservoir end carrying spike 128 and spike cover 130 will be deemed the proximal end and the distal end will be designated the end carrying male luer connector 74. Preferably, a slide clamp 124 is disposed around either first tube section 120 or second tube section 122, permitting the clinician to occlude or close off flow through tubing set 28. In the preferred embodiment, slide clamp 124 is disposed around first tube section 120 and positioned upstream of pump 24.

In the preferred embodiment of the method of the present invention, pump controller 32 is programmed to execute a scrub cycle flushing the endoscope objective lens 54 each time the clinician actuates control switch 38, preferably while mounted on endoscope sheath 26. Scrub cycles are executed in a sequence of method steps including a flush interval with a forward or outflow motion of the pump to dispense a first selected volume of irrigation fluid from reservoir 22 through sheath 26 and over endoscope objective lens 54. A brief pause interval follows, allowing any residual fluid pressure to dissipate, and a suction pulse interval with a reverse or inflow motion of pump 24 next withdraws or retracts any residual fluid droplets from the endoscope objective lens 54 and into the sheath lumen 60. Pump controller 32 is programmed to perform first and second normal scrub cycles followed by a clear or purge cycle, as will be explained in greater detail herein below with reference to the flow chart FIG. 13. The purge cycle differs from the normal scrub cycle in that the duration of the flush interval of the cycle dispensing irrigation fluid over endoscope objective lens 54 is longer than normal at approximately two seconds, thereby flushing any residual body fluids, other surgical debris or air from sheath lumen 60 and restoring optimal lens cleaning system performance.

Pump controller 32 operates to control pump 24 in one of preferably six user selectable modes to determine flush interval forward run times according to a preprogrammed table stored in controller memory 34. Additionally, pump 24 includes a separate control for enabling or disabling the third endoscope clear or purge cycle. Pump controller 32 is also programmed to respond to a continuous purge command selected when control switch 38 is continually depressed and in the closed position longer than the programmed flush interval duration, wherein pump controller 32 is programmed to continually actuate pump 24 to run in the forward mode until such time as control switch 38 is released by the clinician.

In the preferred embodiment, pump controller 32 is responsive to 8-position mode selector switch 36, providing selection of one of six modes of operation for pump 24 corresponding to the preprogrammed operating steps in pump controller 32. The pump modes are OFF, PRIME, MODE 1, MODE 2, MODE 3, MODE 4, MODE 5, and MODE 6.

Pump controller 32 is programmed to illuminate LED 40 at any setting other than "0" or "OFF" under normal conditions. Pump controller 32 executes the method preprogrammed into controller memory 34 and receives and encodes the input of position selector switch 36, thereby placing pump 24 in a mode associated with the selected switch position. As described in greater detail below and set forth in Table I, each pump mode defines a unique scrub cycle including a selected flush interval forward run time and suction pulse interval reverse run time. Pump controller 32 detects the operation of control switch 38 and executes a flush interval upon sensing that control switch 38 has been depressed, continuing pumping in the forward direction for so long as control switch 38 is depressed. When control switch 38 is released, the pump cycle is completed by stopping forward operation of pump motor 42 for the pause interval and then executing the suction pulse interval and operating pump 42 in the reverse direction, as noted above, to draw fluid back and remove residual droplets from the endoscope objective lens 54.

Scrub cycle flush interval forward run time is a function of mode setting, as set forth in Table I:

TABLE I

Pump Run times:

| | | | | |
|---|---|---|---|---|
| (Fwd 1st & 2nd cycle) | Setting 1 | 0.5 s 0.1 s | Setting 2 | 0.75 s 0.1 s |
| (Forward 3rd cycle) | Setting 1 | 1.75 s 0.1 s | Setting 2 | 1.75 s 0.1 s |
| (Fwd 1st & 2nd cycle) | Setting 3 | 1.0 s 0.1 s | Setting 4 | 1.25 s 0.1 s |
| (Forward 3rd cycle) | Setting 3 | 1.75 s 0.1 s | Setting 4 | 1.75 s 0.1 s |
| (Fwd 1st & 2nd cycle) | Setting 5 | 1.5 s 0.1 s | Setting 6 | 1.75 s 0.1 s |
| (Forward 3rd cycle) | Setting 5 | 1.75 s 0.1 s | Setting 6 | 1.75 s 0.1 s |

Scrub cycle suction pulse interval reverse run time is also based on mode setting, according to Table II below.

TABLE II

| | | | | |
|---|---|---|---|---|
| Reverse (Always) | Setting 0 | N/A | Prime | N/A |
| | Setting 1 | 0.25 s 0.075 s | Setting 2 | 0.25 s 0.075 s |
| | Setting 3 | 0.25 s 0.075 s | Setting 4 | 0.50 s 0.1 s |
| | Setting 5 | 0.50 s 0.1 s | Setting 6 | 0.50 s 0.1 s |

Figure 13:
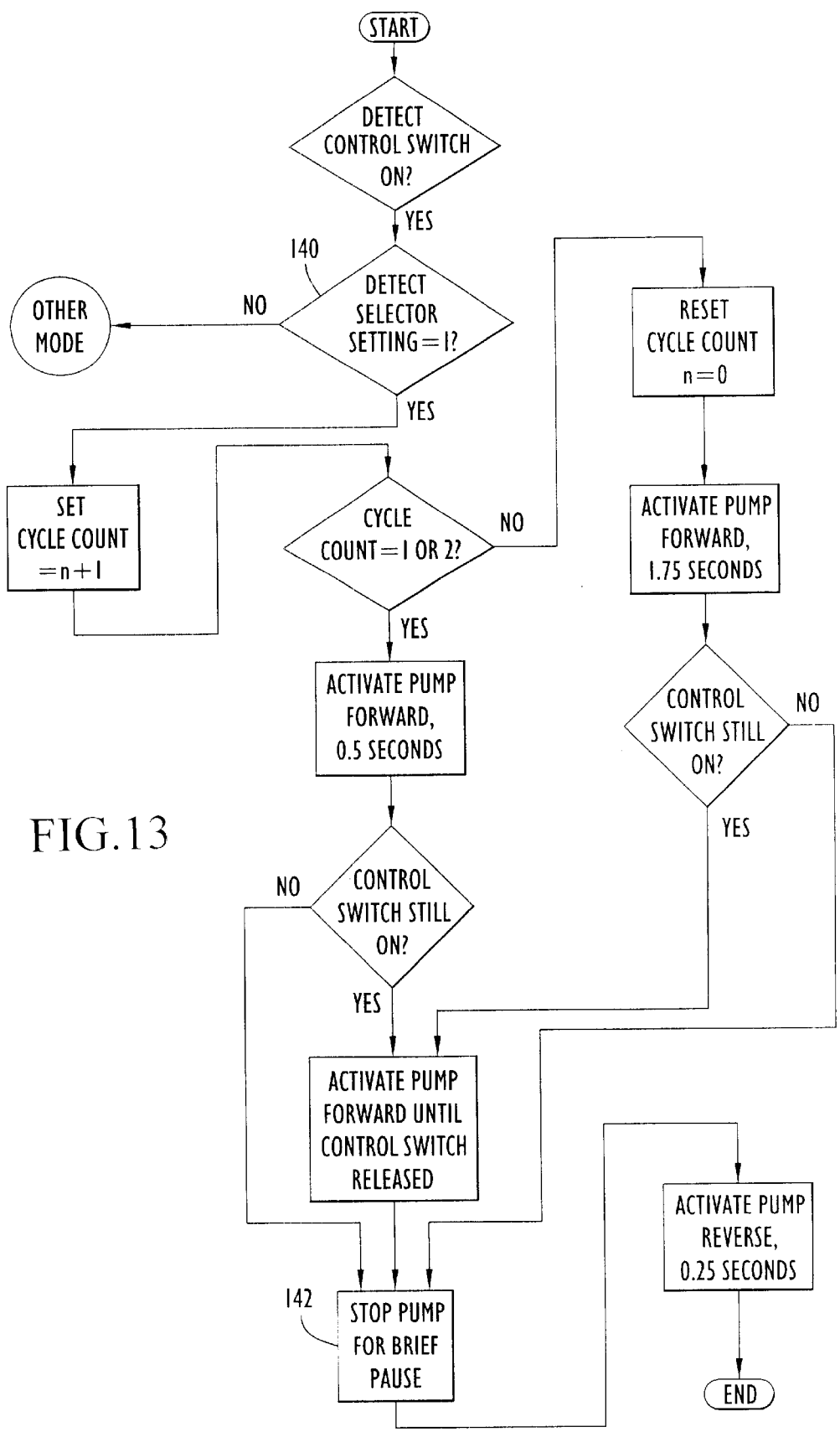
FIG. 13 is a flow chart illustrating method steps for executing a scrub cycle with a flush interval, detection of whether there is to be a purge cycle or continuous purge, a pause interval and suction pulse interval, in accordance with the present invention.

The pump control method of the present invention is implemented in program steps stored in pump controller memory 34 and set forth in greater detail in the flow chart of FIG. 13, illustrating method steps for executing a scrub cycle with a flush interval, detection of whether there is to be a purge cycle or continuous purge, followed by a pause interval and suction pulse interval. It should be noted that FIG. 13 illustrates one illustrative embodiment of the method of the present invention. A first decision block 140 represents a step for detecting when the selector is set to Mode 1 or "Setting 1", as defined in Table I. In the event that the selector setting is other than "Setting 1", then the respective interval durations are adjusted for the other selected mode (e.g., mode 2–mode 6) having different forward and reverse times, as described in Table I. Referring back to FIG. 13, controller 32 first detects whether control switch 38 has been activated and, if so, and if selector switch 36 is set at 1, then the cycle count is incremented. If the cycle count is either 1 or 2, then a normal cleaning cycle is executed rather than the longer purge or endoscope clear cycle and a flush interval is executed wherein pump motor 42 is activated in the forward direction for 0.5 seconds. If control switch 38 remains actuated, then the clinician has signaled that an extended purge cycle is to be executed for so long as control switch 38 is depressed, and pump motor 42 will remain on or actuated until control switch 38 is released. If however, control switch 38 is not on or actuated upon termination of the selected forward run time, then pump motor 42 is stopped for a brief pause interval to allow pressure within sheath lumen 60 to equalize. The pause interval step of block 142 is followed by a suction pulse interval with reverse actuation of pump motor 42 for 0.25 seconds to withdraw fluid into the sheath lumen 60 and clear any droplets from endoscope objective lens 54.

If the cycle count is not equal to 1 or 2, then the cycle count is equal to 3, indicating that a purge cycle of longer duration is now required, in accordance with the method of the present invention. The cycle count is reset and a "purge" flush interval is executed wherein pump motor 42 is activated in the forward direction for the longer interval of 1.75 seconds. As before, the controller 32 must sense whether control switch 38 is still actuated upon completion of the forward run time of 1.75 seconds and, if so, an extended purge cycle is required and pump motor 42 remains activated until control switch 38 is released. After the forward activation of the pump, pump motor 42 is stopped for a brief pause interval and then a suction pulse interval is executed wherein pump 42 is activated in the reverse direction for the selected interval (for mode setting 1) of 0.25 seconds.

As noted above, pump controller 32 also controls indicator LED 40 in a manner to illuminate LED 40 indicating pump status by remaining on whenever pump motor 42 is actuated or by flashing or blinking when an error condition has been sensed. The preprogrammed controller software stored in controller memory 34 also includes method steps for sensing the power bus connected to power supply 44. Power supply 44 is configured to provide uniform energizing signals and control signals to pump motor 42 over a wide range of supply voltages. Pump motor 42 thereby functions at a single selected speed regardless of power bus or mains supply voltage, thereby allowing pump 24 to operate consistently over a wide variety of input power conditions. If, however, the mains supply voltage falls below limits permitting safe operation, pump controller 32 generates an LED flashing signal indicating an operating error.

It will be appreciated in that the embodiments described above and illustrated in the drawings represent only a few of the many ways of implementing the method and apparatus for cleaning an endoscope lens in accordance with the present invention. For example, pump 24 is identified as a peristaltic pump. While peristaltic pump 24 is ideally well suited for use with tubing set 28, in the other pump readily controlled by a microprocessor or microcomputer powered pump controller 32 would be well suited for practicing the method of the present invention. Similarly, while tubing set 28 is, in the preferred embodiment, composed of first tube section 120 joined to second tube section by barb conduit adapter 126, a contiguous and unitary tubing section having a first section of a softer durometer and a second section of a harder durometer would provide a suitable mechanical interface for use with the peristaltic pump while providing a downstream segment of tubing with increased stiffness for greater flow control. Additionally, while the illustrated embodiments employ a rigid endoscope and a substantially rigid endoscope sheath 26, the method and apparatus of the present invention are equally efficacious for use with flexible endoscopes and correspondingly flexible endoscope sheaths.

From the foregoing description that will be appreciated that the invention makes available an improved method and apparatus for cleaning an endoscope lens providing an endoscope lens cleaning system having an endoscope sheath, tubing set and software controlled pump providing the scrub cycle consisting of a forward motion of the pump to dispense irrigation fluid over the endoscope lens, a brief pause to allow any residual pressure to dissipate and a reverse motion of the pump to retract any droplets of fluid remaining on the endoscope lens into the sheath lumen, thereby eliminating the problem of accumulated surgical debris within the sheath lumen and restoring optimal cleaning performance. The method and apparatus of the present invention also makes available an easily connected fluid path permitting the irrigation tubing to be attached to and detached from the sheath quickly and easily when changing endoscopes, as often happens during surgical procedures. The invention further makes available a sheath-mounted, detachable, finger-activated control switch 38 obviating the requirement for an additional foot pedal cluttering the OR floor and providing an intuitive control interface which, using the method and controller software of the present invention, permits the clinician or operator to execute an extended purge cycle without concern for interrupting or interfering with the subsequent operation of the endoscope lens cleaning system.

In as much as the present invention is subject to various modifications and changes in detail, the above description of a preferred embodiment is intended to be exemplary only and not limiting. It is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An endoscope lens cleaning system for removing surgical debris from the objective lens of an endoscope by rinsing the objective lens with irrigation fluid, comprising:
    a momentary contact pump actuation control switch for generating a pump actuation signal when said momentary contact pump actuation control switch is actuated;
    a computer controlled pump; including a pump motor and pump controller; said pump controller being responsive to said control switch pump actuation signal;
    a sheath having a sleeve member terminated proximally in a sleeve housing, said sheath sleeve member having an open proximal end opposite an open distal end and in fluid communication therewith via an interior lumen sized to receive the endoscope;
    said sheath sleeve housing further including a transversely projecting tubular member defining an intersecting transverse fluid lumen in fluid communication with said sheath sleeve interior lumen, said tubular member having an end including a fluid-tight connector;
    a releasably connectable flexible tubing set in fluid communication between said pump and said sheath and having a distal end including a fluid tight connector configured to releasably interlock said sheath fluid tight connector to releasably connect said tubing set to said sheath.

2. The endoscope lens cleaning system of claim 1, further comprising:
    a second sheath sized to receive a differently dimensioned endoscope and having a sleeve member terminated proximally in a sleeve housing, said sheath sleeve member having an open proximal end opposite an open distal end and in fluid communication therewith via an interior lumen sized to receive the endoscope;
    said second sheath sleeve housing further including a transversely projecting tubular member defining an intersecting transverse fluid lumen in fluid communication with said sheath sleeve interior lumen and terminated in a fluid-tight connector.

3. The endoscope lens cleaning system of claim 1, said sheath fluid tight connector comprising a Luer connector female member.

4. An endoscope lens cleaning system for removing surgical debris from the objective lens of an endoscope by rinsing the objective lens with irrigation fluid, comprising:
    a momentary contact pump actuation control switch for generating a pump actuation signal when said momentary contact pump actuation control switch is actuated, said momentary contact pump actuation control switch including a housing with a partial cylindrical wall segment sized to receive and to be releasably mounted on said sheath sleeve housing;
    a computer controlled pump; including a pump motor and pump controller; said pump controller being responsive to said control switch pump actuation signal;
    a sheath having a sleeve member terminated proximally in a sleeve housing, said sheath sleeve member having an open proximal end opposite an open distal end and in fluid communication therewith via an interior lumen sized to receive the endoscope;
    said sheath sleeve housing further including a transversely projecting tubular member defining an intersecting transverse fluid lumen in fluid communication with said sheath sleeve interior lumen and terminated in a fluid-tight connector;
    a releasably connectable flexible tubing set in fluid communication between said pump and said sheath and having a distal end carrying a fluid tight connector releasably connectable with said sheath fluid tight connector.

5. The endoscope lens cleaning system of claim 4, said control switch housing partial cylindrical wall segment including a longitudinal notch sized to receive said sleeve housing transversely projecting tubular member.

6. An endoscope lens cleaning system for removing surgical debris from the objective lens of an endoscope by rinsing the objective lens with irrigation fluid, comprising:
    a momentary contact pump actuation control switch for generating a pump actuation signal when said momentary contact pump actuation control switch is actuated;
    a computer controlled pump; including a pump motor and pump controller; said pump controller being responsive to said control switch pump actuation signal and including a controller memory, said pump being responsive to program steps stored in said controller memory to clean said endoscope lens in a sequence of irrigation fluid pumping steps comprising an irrigation flush interval with a first forward run time followed by a pause interval and a suction pulse interval, said sequence of irrigation fluid pumping steps including a plurality of pre-programmed flush intervals of differing durations;
    a sheath having a sleeve member terminated proximally in a sleeve housing, said sheath sleeve member having an open proximal end opposite an open distal end and in fluid communication therewith via an interior lumen sized to receive the endoscope;

said sheath sleeve housing further including a transversely projecting tubular member defining an intersecting transverse fluid lumen in fluid communication with said sheath sleeve interior lumen and terminated in a fluid-tight connector;

a releasably connectable flexible tubing set in fluid communication between said pump and said sheath and having a distal end carrying a fluid tight connector releasably connectable with said sheath fluid tight connector.

7. The endoscope lens cleaning system of claim 6, said sequence of irrigation fluid pumping steps including a pre-programmed provision to maintain an irrigation flush interval duration lasting for as long as said momentary contact pump actuation control switch remains actuated, followed by a pause interval and a suction pulse interval.

8. An endoscope lens cleaning system for removing surgical debris from the objective lens of an endoscope by rinsing the objective lens with irrigation fluid, comprising:

a momentary contact pump actuation control switch for generating a pump actuation signal when said momentary contact pump actuation control switch is actuated;

a computer controlled pump; including a pump motor and pump controller; said pump controller being responsive to said control switch pump actuation signal;

a sheath having a sleeve member terminated proximally in a sleeve housing, said sheath sleeve member having an open proximal end opposite an open distal end and in fluid communication therewith via an interior lumen sized to receive the endoscope;

said sheath sleeve housing further including a transversely projecting tubular member defining an intersecting transverse fluid lumen in fluid communication with said sheath sleeve interior lumen and terminated in a fluid-tight connector;

a releasably connectable flexible tubing set in fluid communication between said pump and said sheath and having a distal end carrying a fluid tight connector releasably connectable with said sheath fluid tight connector, said releasably connectable flexible tubing set including a first tubing segment of a first selected durometer and a second tubing segment of a second selected durometer greater than said first selected durometer and in fluid communication with said first segment.

9. The endoscope lens cleaning system of claim 8, said second tubing segment distal end carrying said fluid tight connector releasably connectable with said sheath fluid tight connector.

10. An endoscope lens cleaning system for removing surgical debris from the objective lens of an endoscope by rinsing the objective lens with irrigation fluid, comprising:

a sheath having a sleeve member terminated proximally in a sleeve housing, said sheath sleeve member having an open proximal end opposite an open distal end and in fluid communication therewith via an interior lumen irrigation space sized to receive the endoscope;

said sheath sleeve housing further including a transversely projecting tubular member defining an intersecting transverse fluid lumen in fluid communication with said sheath sleeve interior lumen;

a momentary contact pump actuation control switch for generating a pump actuation signal when said momentary contact pump actuation control switch is actuated;

a computer controlled pump in fluid communication with said sheath, said pump including a pump motor and pump controller, said pump controller being responsive to said control switch pump actuation signal;

said momentary contact pump actuation control switch including a housing dimensioned to receive and be releasably mounted on said sheath sleeve housing.

11. The endoscope lens cleaning system of claim 10, said control switch housing including a partial cylindrical wall segment dimensioned to receive and be releasably mounted on said sheath sleeve housing.

12. The endoscope lens cleaning system of claim 11, said control switch housing partial cylindrical wall segment including a longitudinal notch sized to receive said sleeve housing transversely projecting tubular member.

13. The endoscope lens cleaning system of claim 10, said pump controller including a controller memory, said pump being responsive to program steps stored in said controller memory to clean said endoscope lens in a sequence of irrigation fluid pumping steps comprising an irrigation flush cycle with a first forward run time followed by a pause time and a reverse run time;

said sequence of irrigation fluid pumping steps including a plurality of pre-programmed forward run times of differing durations.

14. The endoscope lens cleaning system of claim 13, said sequence of irrigation fluid pumping steps including a pre-programmed provision to maintain a forward run time for so long as said momentary contact pump actuation control switch is actuated, followed by a pause time and a reverse run time.

15. An endoscope lens cleaning system for removing surgical debris from the objective lens of an endoscope by rinsing the objective lens with irrigation fluid, comprising:

a momentary contact pump actuation control switch for generating a pump actuation signal when said momentary contact pump actuation control switch is actuated;

a computer controlled pump; including a pump motor and pump controller; said pump controller being responsive to said control switch pump actuation signal;

said pump controller including a controller memory, said pump being responsive to program steps stored in said controller memory to clean said endoscope lens in a sequence of irrigation fluid pumping steps comprising an irrigation flush cycle with a first forward run time followed by a pause time and a reverse run time;

said sequence of irrigation fluid pumping steps including a plurality of pre-programmed forward run times of differing durations.

16. The endoscope lens cleaning system of claim 15, said sequence of irrigation fluid pumping steps including a pre-programmed provision to maintain a forward run time for so long as said momentary contact pump actuation control switch is actuated, followed by a pause time and a reverse run time.

17. The endoscope lens cleaning system of claim 15, said sequence of irrigation fluid pumping steps including a first forward run time of a first selected duration, followed by a pause time and a reverse run time.

* * * * *